(12) United States Patent
Lu et al.

(10) Patent No.: US 11,338,275 B2
(45) Date of Patent: May 24, 2022

(54) METHOD AND CATALYST FOR PRODUCING BENZYL ALCOHOL AND HOMOLOGUES THEREOF FROM SHORT-CHAIN ALCOHOLS BY CATALYTIC CONVERSION

(71) Applicant: DALIAN UNIVERSITY OF TECHNOLOGY, Liaoning (CN)

(72) Inventors: Anhui Lu, Liaoning (CN); Wencui Li, Liaoning (CN); Baichuan Zhou, Liaoning (CN); Qingnan Wang, Liaoning (CN)

(73) Assignee: DALIAN UNIVERSITY OF TECHNOLOGY, Liaoning (CN)

( * ) Notice: Subject to any disclaimer, the term of this patent is extended or adjusted under 35 U.S.C. 154(b) by 0 days.

(21) Appl. No.: 15/734,879

(22) PCT Filed: Sep. 28, 2018

(86) PCT No.: PCT/CN2018/108265
§ 371 (c)(1),
(2) Date: Dec. 3, 2020

(87) PCT Pub. No.: WO2020/051955
PCT Pub. Date: Mar. 19, 2020

(65) Prior Publication Data
US 2021/0220805 A1    Jul. 22, 2021

(30) Foreign Application Priority Data
Sep. 10, 2018   (CN) .......................... 201811048242.2

(51) Int. Cl.
| | | |
|---|---|---|
| *B01J 27/185* | (2006.01) | |
| *B01J 27/18* | (2006.01) | |
| *B01J 37/02* | (2006.01) | |
| *B01J 37/12* | (2006.01) | |
| *C07C 29/34* | (2006.01) | |

(52) U.S. Cl.
CPC ....... *B01J 27/1853* (2013.01); *B01J 27/1806* (2013.01); *B01J 27/1813* (2013.01); *B01J 27/1817* (2013.01); *B01J 37/0201* (2013.01); *B01J 37/12* (2013.01); *C07C 29/34* (2013.01)

(58) Field of Classification Search
CPC ............... B01J 27/1853; B01J 27/1806; B01J 27/1813; B01J 27/1817; B01J 37/0201; B01J 37/12; B01J 20/048; C07C 29/34; C07C 33/20; C07C 33/22

USPC .................. 502/213; 585/322, 407; 568/905; 423/308, 312
See application file for complete search history.

(56) References Cited

U.S. PATENT DOCUMENTS

| | | | | |
|---|---|---|---|---|
| 5,545,791 A | * | 8/1996 | Sakuma ................... | B01J 27/16 585/638 |
| 5,723,401 A | * | 3/1998 | Sakuma ................... | B01J 27/16 502/208 |
| 10,960,386 B2 | * | 3/2021 | Lu ......................... | B01J 27/1856 |
| 2014/0235902 A1 | * | 8/2014 | Morvan ................ | C07C 29/172 568/909.5 |

FOREIGN PATENT DOCUMENTS

| | | | |
|---|---|---|---|
| CN | 101544627 A | 9/2009 | |
| CN | 102989490 A | 3/2013 | |
| CN | 104024194 A | 9/2014 | |
| CN | 107001215 A | 8/2017 | |
| CN | 107626349 A | 1/2018 | |
| CN | 108117480 * | 6/2018 | ............. C08C 29/34 |
| CN | 109111343 A | 1/2019 | |

OTHER PUBLICATIONS

Translation of Written Opinion for PCT/CN2018/108265. (Year: 2019).*

* cited by examiner

*Primary Examiner* — Patricia L. Hailey
(74) *Attorney, Agent, or Firm* — Muncy, Geissler, Olds & Lowe, P.C.

(57) ABSTRACT

Methods and catalysts for producing benzyl alcohol and homologues thereof from short-chain alcohols by catalytic conversion are disclosed. The methods and catalysts develop a new route for benzyl alcohols and ethyl benzyl alcohols production through cross coupling-aromatization reaction using short-chain alcohols as reactants and provide corresponding catalysts required for the above catalytic reaction. It is emphasized on a single bed catalyst to produce benzyl alcohol and its homologues in one step, and is expected to become an important alternative route for the production of benzyl alcohol and its homologues. A route and corresponding catalysts for directly producing benzyl alcohol and ethyl benzyl alcohol through coupling-aromatization reaction starting from low carbon alcohols are provided. The selectivity of the benzyl alcohol is up to 35%, and the total selectivity of the ethyl benzyl alcohol is up to 11%.

5 Claims, No Drawings

METHOD AND CATALYST FOR PRODUCING BENZYL ALCOHOL AND HOMOLOGUES THEREOF FROM SHORT-CHAIN ALCOHOLS BY CATALYTIC CONVERSION

TECHNICAL FIELD

The present invention relates to method and catalyst for producing benzyl alcohol and homologues thereof from short-chain alcohols by catalytic conversion, and belongs to the field of chemical engineering and technology.

BACKGROUND

Benzyl alcohol is an indispensable edible spice, and is widely applied in the fields of medicine and cosmetics. Derivatives of ethyl benzyl alcohol can be used to produce baked, jam/gel and nut food. At present, the production methods of benzyl alcohol mainly include toluene chlorination-hydrolysis or its catalytic oxidation. At present, the toluene chlorination-hydrolysis is a main method for producing benzyl alcohol in industry. However, the chlorination reaction of toluene is not easy to control. A large number of polychlorinated products are easy to excessively hydrolyze in acid solutions. The reaction products are mainly benzoic acid and benzaldehyde, causing low selectivity (<5%) of the target product [Chloralkali Industry, 2004, 8, 29]. In the toluene catalytic oxidation, the obtained target product is further oxidized under harsh oxidation conditions to produce a large amount of aldehyde and acid derivatives, causing low selectivity (2%) of benzyl alcohol [Chinese Patent CN107626349 A]. Ethyl benzyl alcohol is obtained from of ethyl toluene by selective oxidation. Toluene and ethyl toluene are produced by steam cracking or catalytic reforming, separation and purification of naphthol derived from petroleum. However, the target products shift of the oil refinery to gasoline, causing global shortage of aromatic feedstocks [Science 2014, 344, 616; Angew. Chem. Int. Ed. 2013, 52, 11980]. Therefore, it is urgent to develop a route to produce benzyl alcohol and ethyl benzyl alcohol from sustainable resources directly.

The availability of short-chain alcohols such as methanol, ethanol and propanol is further increased on basis of the industrialization of low-carbon alcohol production from syngas and through biomass fermentation. The methanol in China has an output of up to 43.58 million tons (in 2014); ethanol has an output of up to 15 million tons (in 2015); and propanol has an output of about up to 190,000 tons (in 2014). Short-chain alcohols as raw materials can be converted into oxygen-containing chemicals with odd number of carbon atoms (C$\geqslant$3) through cross C-C coupling reaction. However, the currently reported catalysts show poor selectivity for high chain products, because of the co-existence of several complicated competition reactions during the carbon chain growth process. There is no report of producing aromatic oxygen-containing compounds [Catal. Sci. Technol., 2015, 5, 3876]. The development of a route for direct conversion of short-chain alcohols to benzyl alcohol and ethyl benzyl alcohol possibly meets the urgent demand for sustainable energy and then, can possibly replace, or partially, the petroleum-based route. On the other hand, a direct production technology also contributes to alleviate aromatics imbalance between supply and demand and is of great significance to ensure the safety and stability of economic construction and development in China.

SUMMARY

The purpose of the present invention is to develop a green and sustainable route of producing benzyl alcohol and ethyl benzyl alcohol through cross coupling-aromatization reaction using methanol+ethanol or ethanol+propanol as mixed raw materials and provide corresponding catalysts required for the aboved catalytic reaction. The present invention emphasizes on a single bed catalyst to produce benzyl alcohol and its homologues in one-step, and is expected to become an important alternative route for aromatic alcohols production.

Reaction equations are as follows:

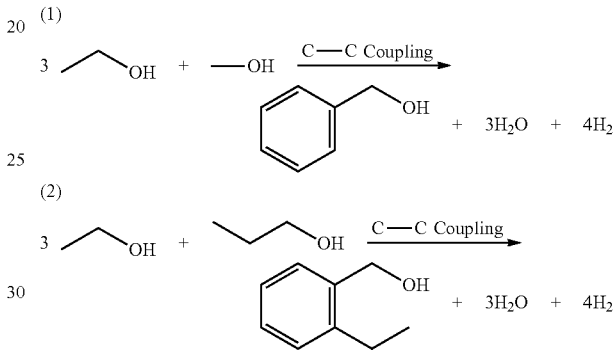

This innovative reaction route for benzyl alcohol and its homologues from low carbon alcohol has several advantages, such as high atom economy, eco-friendly property, and easy separation of products, as compared with a traditional petroleum-based route. This present reaction route has a reaction temperature of 150-450° C., selectivity of 35% for benzyl alcohol and total selectivity of 11% for ethyl benzyl alcohol, and has good industrial application prospect.

The technical solution of the present invention is:

A method for producing benzyl alcohol and homologues thereof from short-chain alcohols by catalytic conversion comprises the following steps:

(1) Preparing transition metals aqueous solution and/or transition metals alcohol solution with a certain concentration;

(2) Using an incipient wetness impregnation method to impregnate hydroxyl phosphates using the transition metals aqueous solution and/or transition metals alcohol solution prepared in the step (1); after impregnation, stayed at room temperature for 0.5-2 h;

(3) Placing the obtained mixtures from the step (2) into a 100° C. oven for drying for 8-20 h;

(4) Conducting oxidation on the dried product in the step (3) at 250-550° C. for 1 to 5 h in an air atmosphere, and then treating under a hydrogen atmosphere at 325-700° C. for 0.5-2 h to obtain transition metal-hydroxyl phosphate catalysts;

(5) at reaction temperature of 150-450° C. and reaction pressure of 1-50 atm, introducing mixture of ethanol and methanol or mixture of ethanol and propanol into a reactor packed with transition metal-hydroxyl phosphate catalysts to produce benzyl alcohol or ethyl benzyl alcohol by one-pot synthesis through coupling-aromatization reaction.

In the step (1), the concentration of the transition metals aqueous solution is 0.08 g/mL-0.75 g/mL; the concentration of the transition metals alcohol solution is 0.08-0.3 g/mL; soluble salts of transition metals are selected from one or a combination of more than one of chloride, nitrate, levulinate, sulfate and acetate; the alcohol solvent is selected from methanol and/or ethanol.

In the step (4), the concentration of hydrogen atmosphere is one of 5-20 vol % $H_2/N_2$, 5-20 vol % $H_2/He$ and 5-20 vol % $H_2/Ar$.

The catalyst is transition metal-hydroxyl phosphate, and comprises the following components by weight percent:

(1) transition metals are selected from one or a combination of more than one of Co, Ni, Cu, Ag, Ir, Zn and Y; the transition metals are in an oxidation state or a metal state; nitrate, chloride, levulinate, sulfate or acetate of the transition metals is adopted as a precursor; loading is 0.01-50 wt % of the weight of the hydroxyl phosphate;

(2) the chemical formula of hydroxyl phosphate is $A_xB_yC_zD_mE_n(OH)_2(PO_4)_6$; in the formula, $x+y+z+m+n=9-10$, $9-10 \geq x,y,z,m,n \geq 0$, wherein A, B, C, D and E are the same or different and are selected from one or a combination of more than one of Mg, Ca, Sr, Ba and Pb; the hydroxyl phosphate is one or a mechanical mixture of more than one.

The transition metal is preferably Co with loading of 0.01-50 wt % on basis of hydroxyl phosphate, and preferably 0.1-5 wt %.

The hydroxyl phosphate is preferably $Ca_{10}(OH)_2(PO_4)_6$, and additionally preferably an atmospheric fix-bed reactor.

Beneficial effects of the present invention, as compared with the current production technology, the present invention provides a route and corresponding catalysts for directly producing benzyl alcohol and ethyl benzyl alcohol through coupling-aromatization reaction starting from low carbon alcohols. The selectivity of the benzyl alcohol is up to 35%, and the total selectivity of the ethyl benzyl alcohol is up to 11%. This innovative reaction route produces hydrogen as co-product, and can be directly used in chemical reactions and fuel cells. In addition, the route also produces high carbon number ($C_{3-8}$) alcohols which can be used as fuels or oil additives to partially replace petroleum-based products, thus partly reducing the dependence on petroleum. It is of great strategic significance to energy security. In addition, the benzyl alcohol or ethyl benzyl alcohol and high carbon number aliphatic alcohols are easy to be separated via a distillation technology with low post-treatment cost. Therefore, the presented reaction route has great commercial application prospect.

DETAILED DESCRIPTION

The present invention is described below in detail through some embodiments. However, the present invention is not limited to these embodiments.

The hydroxyl phosphate is represented by HAP-M, wherein
HAP represents hydroxymetallic apatite; and M refers to metal and is one or more of Mg, Ca, Sr, Ba, Pb, etc.

The catalysts are represented by xMetal-HAP-M, wherein $x$=weight percent of metal loading in total weight of the catalysts×100.

Embodiment 1

Synthesis of Co-HAP-Ca Catalyst:

(1) HAP-Ca is dried at 120° C. for 2 h in an airflow oven to remove physical adsorption water on its surface;

(2) Catalyst mixture are prepared via an incipient wetness impregnation method via treating the HAP-Ca dried in the step (1) at 25° C. using $Co(NO_3)_2$ aqueous solution prepared in entry 3 in Table 1, and stayed for 2 h;

(3) The obtained mixture after staying in step (2) is then dried at 100° C. for 10 h under the air atmosphere to obtain corresponding catalyst precursors;

(4) The catalyst precursor obtained in the step (3) is further oxidized at 350° C. for 2 h in the air atmosphere, and then subjected reduction treatment at 400° C. for 2 h (10 vol % $H_2/N_2$) to obtain Co-HAP-Ca, which was denoted as Co-HAP-Ca (entry 3 in Table 1);

(5) The loading of Co can be changed by controlling metal salt concentration and impregnation time, with the preparation method the same as the above steps, corresponding to entries 2, 3, and 4 in Table 1.

The preparation conditions of other catalysts are the same as these in embodiment 1. The corresponding relationship between the sample number and the preparation conditions are shown in Table 1.

TABLE 1

Corresponding Relationship between Sample Number and Preparation Conditions in Embodiment 1

| Entry | Catalyst | Loading/wt % | Support | Metals | Solvent | Concentration/g/mL | Temperature /° C. |
|---|---|---|---|---|---|---|---|
| 1 | HAP-Ca | 0 | HAP-Ca | Cobalt nitrate | Water | 0 | 400 |
| 2 | 0.1Co-HAP-Ca | 0.1 | HAP-Ca | Cobalt nitrate | Water | 0.1 | 400 |
| 3 | 1.6Co-HAP-Ca | 1.6 | HAP-Ca | Cobalt nitrate | Water | 0.75 | 400 |
| 4 | 8.9Co-HAP-Ca | 8.9 | HAP-Ca | Cobalt nitrate | Water | 0.75 | 400 |
| 5 | 1.6Co-HAP-Sr | 0.8 | HAP-Sr | Cobalt nitrate | Water | 0.5 | 400 |
| 6 | 1.6Co-HAP-Mg | 0.8 | HAP-Mg | Cobalt nitrate | Water | 0.5 | 400 |
| 7 | 1.6Co-HAP-Ba | 0.8 | HAP-Ba | Cobalt nitrate | Water | 0.75 | 400 |

TABLE 1-continued

Corresponding Relationship between Sample Number and Preparation Conditions in Embodiment 1

| Entry | Catalyst | Loading/ wt % | Support | Metals | Solvent | Concentration/ g/mL | Temperature /° C. |
|---|---|---|---|---|---|---|---|
| 8 | 1.6Co-HAP-Pb | 0.8 | HAP-Pb | Cobalt nitrate | Water | 0.5 | 400 |
| 9 | 1.6Co-HAP-Ca/Sr | 0.8 | HAP-Ca/Sr | Cobalt nitrate | Water | 0.5 | 400 |
| 10 | 1.6Co-HAP-Ca/Sr/Ba | 0.8 | HAP-Ca/Sr/Ba | Cobalt nitrate | Water | 0.5 | 400 |
| 11 | 1.6Co-HAP-Ca + 1.6Ni-HAP-Ca | 0.8 | HAP-Ca | Cobalt nitrate | Water | 0.5 | 400 |
| 12 | 1.6Co-HAP-Ca | 0.8 | HAP-Ca | Cobalt chloride | Water | 0.5 | 400 |
| 13 | 1.6Co-HAP-Ca | 0.8 | HAP-Ca | Cobalt acetate | Water | 0.5 | 400 |
| 14 | 1.6Ni-HAP-Ca | 0.8 | HAP-Ca | Nickel nitrate | Water | 0.5 | 500 |
| 15 | 0.3Cu-HAP-Ca | 0.8 | HAP-Ca | Copper nitrate | Water | 0.5 | 400 |
| 16 | 0.8Ag-HAP-Ca | 0.8 | HAP-Ca | Silver nitrate | Water | 0.5 | 400 |
| 17 | 0.8ZnO-HAP-Ca | 0.8 | HAP-Ca | Zinc nitrate | Water | 0.5 | 400 |
| 18 | 0.5Co0.5ZnO-HAP-Ca | 0.8 | HAP-Ca | Cobalt nitrate + Nickel nitrate | Water | 0.3 | 400 |
| 19 | 1.6Co-HAP-Ca | 0.8 | HAP-Ca | Cobalt nitrate | Ethanol | 0.3 | 400 |
| 20 | 1.6Co-HAP-Ca | 0.8 | HAP-Ca | Cobalt nitrate | Methanol | 0.3 | 400 |

Embodiment 2

Synthesis of Co and ZnO-HAP—Ca-Based Catalyst:

(1) HAP-Ca is dried at 120° C. for 2 h in an airflow oven to remove physical adsorption water on its surface;

(2) At 25° C., the $Co(NO_3)_2$ aqueous solution prepared in entry 3 in Table 1 and the $Zn(NO_3)_2$ aqueous solution prepared in entry 17 are mixed at equal volume; and then, an incipient wetness impregnation method is used to treat the HAP-Ca dried in the step (1) to stand for 2 h;

(3) the obtained mixture after staying in step (2) is then dried at 100° C. for 10 h under the air atmosphere to obtain corresponding catalyst precursors;

(4) the catalyst precursor obtained in the step (3) is oxidized at 350° C. for 2 h in the air atmosphere, and then subjected to hydrogen reduction at 450° C. for 2 h (10 vol % $H_2/N_2$) to obtain Co and ZnO-HAP-Ca catalyst, which is denoted as CoZnO-HAP-Ca (entry 18 in Table 1) catalyst.

Embodiment 3

Several transition metal-hydroxyl phosphate catalyze the conversion of ethanol and methanol to benzyl alcohol.

the coupling and aromatization of ethanol and methanol is conducted in a fix-bed, atmosphere pressure reactor by co-feeding ethanol and methanol. The used catalyst is first packed in the fix-bed reactor with an inner diameter of 8 mm and kept at 300° C. Then, liquid ethanol is fed in a rate of 0.1 mL/h; and methanol liquid is fed in a rate of 0.2 mL/h. After steady, the product distributions are analyzed by an on-line gas chromatography (GC). The corresponding relationship between sample number and catalytic activity is shown in Table 2.

TABLE 2

Corresponding Relationship between Sample Number and Ethanol and Methanol Conversion and Benzyl Alcohol Selectivity in Embodiment 3

| Entry | Catalyst | Ethanol conversion | Methanol conversion | Selectivity/% |
|---|---|---|---|---|
| 1 | HAP-Ca | 18.1 | 3.2 | 0.1 |
| 2 | 0.1Co-HAP-Ca | 19.3 | 3.8 | 3.3 |
| 3 | 1.6Co-HAP-Ca | 22.1 | 5.7 | 35.2 |
| 4 | 8.9Co-HAP-Ca | 25.9 | 5.5 | 25.5 |
| 5 | 1.6Co-HAP-Sr | 24.9 | 4.9 | 29.1 |
| 6 | 1.6Co-HAP-Mg | 20.2 | 3.8 | 25.8 |
| 7 | 1.6Co-HAP-Ba | 26.6 | 4.2 | 19.0 |
| 8 | 1.6Co-HAP-Pb | 28.6 | 3.2 | 12.5 |
| 9 | 1.6Co-HAP-Ca/Sr | 25.5 | 5.5 | 30.5 |
| 10 | 1.6Co-HAP-Ca/Sr/Ba | 25.5 | 5.6 | 29.2 |
| 11 | 1.6Co-HAP-Ca + 1.6Ni-HAP-Ca | 24.1 | 5.1 | 25.0 |
| 12 | 1.6Co-HAP-Ca | 20.1 | 4.8 | 26.2 |
| 13 | 1.6Co-HAP-Ca | 19.8 | 4.6 | 25.2 |
| 14 | 1.6Ni-HAP-Ca | 22.2 | 4.3 | 20.1 |
| 15 | 0.3Cu-HAP-Ca | 25.0 | 7.8 | 19.8 |
| 16 | 0.8Ag-HAP-Ca | 16.0 | 5.4 | 20.8 |
| 17 | 0.8ZnO-HAP-Ca | 26.2 | 5.2 | 32.0 |
| 18 | 0.5Co0.5ZnO-HAP-Ca | 20 | 5.3 | 34.2 |
| 19 | 1.6Co-HAP-Ca | 17.2 | 4.5 | 25.5 |
| 20 | 1.6Co-HAP-Ca | 22.1 | 4.5 | 21.0 |

Embodiment 4

Effect of the Partial Pressure of Ethanol and Methanol on Selectivity of Benzyl Alcohol with Co-HAP-Ca Catalysts The coupling and aromatization of ethanol and methanol is conducted in a fix-bed, atmosphere pressure reactor by feeding ethanol and methanol. Reaction conditions are as follows: the catalyst is first packed in the fix-bed reactor with an inner diameter of 8 mm at 1 atm pressure and reaction temperature of 300° C. The total partial pressure of ethanol and methanol is 6 kPa. The relative ratio of ethanol and methanol is adjusted by controlling the flow rate of the ethanol and methanol. After steady, the reaction reactants and products are analyzed by an on-line gas chromatography (GC). Table 3 shows the ethanol and methanol conversion and the selectivity of benzyl alcohol under different partial pressures.

TABLE 3

Effect of Relative Partial Pressure of Ethanol and Methanol of Embodiment 4 on Selectivity of Benzyl Alcohol

| Ethanol (kPa) | Methanol (kPa) | Ethanol conversion | Methanol conversion | Selectivity/% |
|---|---|---|---|---|
| 6 | 0 | 18.1 | / | 0 |
| 4 | 2 | 12.5 | 6.5 | 10.3 |
| 3 | 3 | 17.6 | 6.3 | 21.6 |
| 2 | 4 | 22.1 | 5.7 | 35.2 |
| 1 | 5 | 29.6 | 8.5 | 35.1 |

Embodiment 5

Several transition metal-hydroxyl phosphate catalysts are used to catalyze the conversion of ethanol and propanol to ethyl benzyl alcohol.

Ethanol and propanol coupling-aromatization reaction is conducted in a fix-bed, atmosphere pressure reactor by feeding ethanol and propanol as reactants. Reaction conditions are as follows: the catalyst is first packed in the fix-bed reactor with an inner diameter of 8 mm and kept at 300° C. Then, ethanol liquid is fed in a rate of 0.1 mL/h; and propanol liquid is fed in a rate of 0.1 mL/h. After steady, the reaction reactants and products are analyzed by an on-line gas chromatography (GC). The corresponding relationship between sample number and catalytic activity is shown in Table 4.

TABLE 4

Corresponding Relationship between Sample Number and Ethanol and Propanol Conversion and Ethyl Benzyl Alcohol Selectivity in Embodiment 5

| Entry | Catalyst | Ethanol conversion/% | Propanol conversion/% | Selectivity/% |
|---|---|---|---|---|
| 1 | HAP-Ca | 15.1 | 5.2 | 0.1 |
| 2 | 0.1Co-HAP-Ca | 16.3 | 5.8 | 2.3 |
| 3 | 1.6Co-HAP-Ca | 18.7 | 6.7 | 11.2 |
| 4 | 8.9Co-HAP-Ca | 15.7 | 5.5 | 8.5 |
| 5 | 1.6Co-HAP-Sr | 14.9 | 4.9 | 9.1 |
| 6 | 1.6Co-HAP-Mg | 13.2 | 4.8 | 8.7 |
| 7 | 1.6Co-HAP-Ba | 17.1 | 5.1 | 7.9 |
| 8 | 1.6Co-HAP-Pb | 16.6 | 4.9 | 7.5 |
| 9 | 1.6Co-HAP-Ca/Sr | 15.5 | 5.0 | 9.5 |
| 10 | 1.6Co-HAP-Ca/Sr/Ba | 14.9 | 5.4 | 10.2 |
| 11 | 1.6Co-HAP-Ca + 1.6Ni-HAP-Ca | 15.1 | 5.1 | 9.0 |
| 12 | 1.6Co-HAP-Ca | 16.1 | 4.8 | 6.2 |
| 13 | 1.6Co-HAP-Ca | 15.8 | 4.6 | 5.2 |
| 14 | 1.6Ni-HAP-Ca | 19.2 | 7.3 | 8.1 |
| 15 | 0.3Cu-HAP-Ca | 20.0 | 6.8 | 3.8 |
| 16 | 0.8Ag-HAP-Ca | 16.0 | 5.4 | 8.8 |
| 17 | 0.8ZnO-HAP-Ca | 16.2 | 5.2 | 9.0 |
| 18 | 0.5Co0.5ZnO-HAP-Ca | 20 | 5.3 | 10.2 |
| 19 | 1.6Co-HAP-Ca | 17.2 | 5.5 | 7.5 |
| 20 | 1.6Co-HAP-Ca | 21.1 | 4.5 | 9.0 |

Embodiment 6

Effect of the partial pressure of ethanol and propanol on selectivity of ethyl benzyl alcohol with Co-HAP-Ca catalysts.

Ethanol and propanol coupling-aromatization reaction is conducted in a fix-bed, atmosphere pressure reactor by feeding ethanol and propanol as reactants. Reaction conditions are as follows: the catalyst is first packed in the fix-bed reactor with an inner diameter of 8 mm at normal pressure and reaction temperature of 300° C. The total partial pressure of ethanol and propanol is 6 kPa. The relative ratio of ethanol and propanol is adjusted by controlling the feed flow rate of the ethanol and propanol.

TABLE 5

Effect of Relative Partial Pressure of Ethanol and Propanol of Embodiment 6 on Selectivity of Ethyl Benzyl Alcohol

| Ethanol/ kPa | Propanol/ kPa | Ethanol conversion/ % | Propanol conversion/ % | Selectivity/% |
|---|---|---|---|---|
| 6 | 0 | 18.3 | / | 0 |
| 4 | 2 | 12.7 | 4.2 | 3.5 |
| 3 | 3 | 16.6 | 5.5 | 8.1 |
| 2 | 4 | 18.7 | 6.2 | 11.2 |
| 1 | 5 | 30.9 | 10.3 | 11.3 |

The invention claimed is:

1. A method for producing benzyl alcohol or ethyl benzyl alcohol thereof from short-chain alcohols by catalytic conversion, comprising the following steps:
    (1) preparing transition metals aqueous solution and/or transition metals alcohol solution;
    (2) using an incipient wetness impregnation method to impregnate hydroxyl phosphates using the transition metals aqueous solution and/or transition metals alcohol solution prepared in the step (1); after impregnation, stayed at room temperature for 0.5-2 h;
    (3) placing the obtained mixture from the step (2) into a 100° C. oven for drying for 8-20 h;
    (4) conducting oxidation on the dried product in the step (3) at 250-550° C. for 1 to 5 h in an air atmosphere, and then treating under hydrogen atmosphere at 325-700° C. for 0.5-2 h to obtain transition metal-hydroxyl phosphate catalysts;
    wherein the transition metal-hydroxyl phosphate catalysts comprise two parts: transition metals and hydroxyl phosphate; loading of the transition metals is 0.01-50 wt % of the weight of the hydroxyl phosphate;
    the transition metals are one or a combination of more than one of Co, Ni, Cu, Ag, Ir, Zn and Y;
    the hydroxyl phosphate is $A_xB_yC_zD_mE_n(OH)_2(PO_4)_6$; in the formula, x+y+z+m+n=9-10, 9-10≥ x,y,z,m,n≥ 0, wherein A, B, C, D and E are the same or different and are selected from one or a combination of more than one of Mg, Ca, Sr, Ba and Pb;
    (5) at reaction temperature of 150-450 ° C. and reaction pressure of 1-50 atm, introducing mixture of ethanol and methanol or mixture of ethanol and propanol into a reactor packed with the transition metal-hydroxyl phosphate catalysts to produce benzyl alcohol or ethyl benzyl alcohol by one-pot synthesis through a designed coupling-aromatization reaction.

2. The method according to claim 1, wherein in the step (1), the concentration of the transition metals aqueous solution is 0.08 g/mL-0.75 g/mL; the concentration of the transition metals alcohol solution is 0.08-0.3 g/mL.

3. The method according to claim 1, wherein corresponding soluble salts of transition metals are one or mixture of more than one of chloride, nitrate, levulinate, sulfate and acetate; the alcohol solvent is selected from methanol and/or ethanol.

4. The method according to claim 3, wherein in the step (4), the concentration of hydrogen atmosphere is one of 5-20 vol % $H_2/N2$ or $H_2/He$ or $H_2/Ar$.

5. The method according to claim 1, wherein in the step (4), the concentration of hydrogen atmosphere is one of 5-20 vol% $H_2/N_2$ or $H_2/He$ or $H_2/Ar$.

* * * * *